United States Patent [19]

Kikumoto et al.

[11] Patent Number: 4,684,739

[45] Date of Patent: Aug. 4, 1987

[54] ALKYLENEDIOXYBENZENE DERIVATIVES AND ACID ADDITION SALTS THEREOF

[75] Inventors: Ryoji Kikumoto, Machida; Harukazu Fukami, Yokohama; Kenichiro Nakao; Mamoru Sugano, both of Tokyo, all of Japan

[73] Assignee: Mitsubishi Chemical Industries Limited, Tokyo, Japan

[21] Appl. No.: 326,417

[22] Filed: Dec. 1, 1981

[30] Foreign Application Priority Data

Dec. 15, 1980 [JP] Japan ................................. 55-176910
Dec. 25, 1980 [JP] Japan ................................. 55-184290
Aug. 7, 1981 [JP] Japan ................................. 56-123817
Aug. 11, 1981 [JP] Japan ................................. 56-125813

[51] Int. Cl.⁴ .................. C07D 319/20; C07D 321/10
[52] U.S. Cl. ..................................... 549/350; 549/366
[58] Field of Search ..................... 260/340.3; 549/366, 549/350

[56] References Cited

U.S. PATENT DOCUMENTS

| | | | |
|---|---|---|---|
| 2,695,294 | 11/1954 | Swain | 544/377 |
| 3,324,000 | 6/1967 | Judd | 424/278 |
| 3,324,143 | 6/1967 | Moed et al. | 424/278 |
| 3,681,393 | 8/1972 | Jonas et al. | 424/278 |
| 4,085,221 | 4/1978 | Smith | 424/275 |

*Primary Examiner*—Nicky Chan
*Attorney, Agent, or Firm*—Oblon, Fisher, Spivak, McClelland & Maier

[57] ABSTRACT

Alkylenedioxybenzene derivatives are prepared and found to be useful as pharmaceutical agents, particularly as hypotensives.

12 Claims, No Drawings

ALKYLENEDIOXYBENZENE DERIVATIVES AND ACID ADDITION SALTS THEREOF

BACKGROUND OF THE INVENTION

Field of the Invention

This invention relates to alkylenedioxybenzene derivatives and acid addition salts thereof having hypotensive activities.

SUMMARY OF THE INVENTION

The compounds according to this invention are represented by the formula (I):

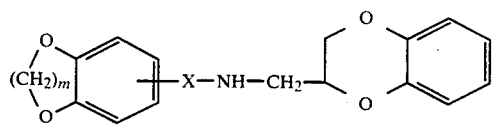

wherein X is a group of the formula: $-Z-(CH_2)_n-$ wherein Z is $-OCH_2-$,

where R is hydrogen, $C_1-C_3$ alkyl or $-COR'$ (where R' is hydrogen or $C_1-C_3$ alkyl), $-NHCO-$ or $-S(O)lC-H_2-$ where $l$ is 0, 1 or 2, and n is 2 or 3; $-(CH_2)_4-$;

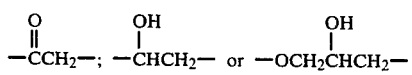

and m is an integer of 1 to 3.

Also encompassed within this invention are acid addition salts thereof.

The compounds of this invention can be used effectively as hypotensives.

DESCRIPTION OF THE PREFERRED EMBODIMENTS

As summarized above, this invention relates to a group of the compounds useful as hypotensives, the structure is as follows:

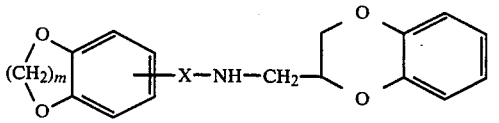

In the above formula (I), X is a group of the formula: $-Z-(CH_2)_n-$ where Z is $-OCH_2-$,

where R is hydrogen, $C_1-C_3$ alkyl or $-COR'$ (where R' is hydrogen or $C_1-C_3$ alkyl), $-NHCO-$ or $-S(O)lC-H_2-$ where $l$ is 0, 1 or 2, and n is 2 or 3; $-(CH_2)_4-$;

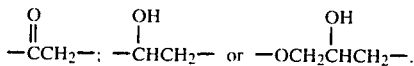

In the formula (I), the position of the substituent:

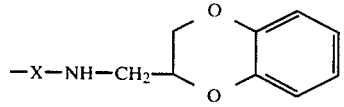

on the dioxybenzene ring is not limited. The compounds according to this invention may be prepared by the following processes:

Process 1

The compounds of Formula (I) wherein X is $-Z-(CH_2)_n-$ [where Z is $-OCH_2-$,

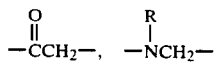

where R is hydrogen, $C_1-C_3$ alkyl or $-COR'$ (R' is hydrogen or $C_1-C_3$ alkyl) or $-S(O)lCH_2-$ ($l$ is 0, 1 or 2), and n is an integer of 2 or 3], $-(CH_2)_4-$ or

may be prepared by reacting a halogen-substituted alkylenedioxybenzene derivative of the formula:

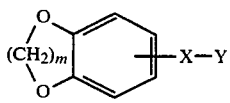

wherein m is as defined in Formula (I) above and Y is a halogen atom, with an amine of the formula:

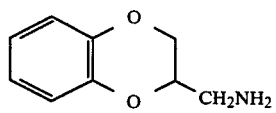

The halogene-substituted alkylenedioxybenzene derivative and the amine react at a molar ratio of 1:1. However, the amine is preferably used in excess, since under such conditions the reaction usually proceeds more smoothly. Thus, the amine may be used in an amount of 1 to 10 moles per mole of the halogene-substituted alkylenedioxybenzene derivative.

While the reaction proceeds well even in the absence of solvents, an inert solvent may be used to allow the reaction to proceed more smoothly. Useful solvents include water, dioxane, tetrahydrofuran, dimethylformamide, dimethylsulfoxide, lower alcohols and a mixture of two or more of these solvents.

The reaction temperature is not critical and it is usually from $-10°$ C. to 150° C., preferably from 0° C. to 100° C.

The reaction time depends on the reaction temperature, the reactivities of the starting materials and the particular solvent, if it is used, and it is usually within the range of 10 minutes to 50 hours.

A base may be added to bind the hydrogen halide formed by the reaction, thereby accerelating the reaction. The base useful for this purpose includes inorganic base materials such as potassium hydroxide, potassium carbonate, sodium hydroxide, sodium hydrogen carbonate, sodium carbonate, etc., as well as organic tertiary amines such as pyridine, triethylamine, etc. The base is usually used in an amount of 1 to 5 moles per mole of the amine of Formula (III).

An acid addition salt of the compound (I) may be prepared from the reaction mixture by removing therefrom the excess amine(s) and the solvent, if present, by distillation or washing with water, and then adding an aqueous solution of a strong base such as sodium hydroxide or potassium hydroxide to give the free alkylenedioxybenzene derivative, which is then extracted into a suitable organic solvent such as ether, chloroform, benzene, toluene or the like.

The separated organic layer is neutralized by addition of the appropriate acid to give the desired acid addition salt.

Process 2

The compounds of Formula (I) wherein X is

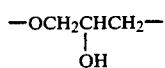

may be prepared in the same manner as described in Process 1 above except that the compound of Formula (II) used in the above-mentioned reaction is replaced by an epoxide of the formula:

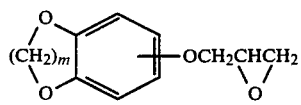 (IV)

wherein m is as defined in Formula (I) above.

The epoxide (IV) which is one of the starting compounds may be obtained by reacting a compound of the formula:

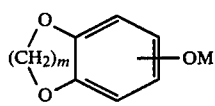 (V)

wherein m is as defined in Formula (I) above and M is an alkali metal, with epichlorohydrin in an aprotic solvent such as dimethylformamide.

Process 3

The compounds of Formula (I) wherein X is

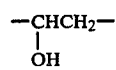

may be prepared by treating a compound of the formula:

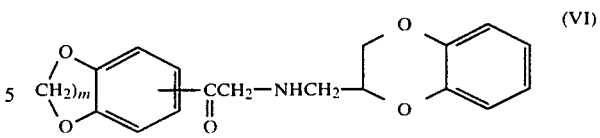 (VI)

wherein m is as defined in Formula (I) above, which is obtained by the reaction described in Process 1, either as it is or after its acid addition salt has been neutralized, with a metal hydride such as sodium borohydride in a solvent such as water, a lower alcohol (e.g., methanol, ethanol) or a mixture thereof.

Process 4

The compounds of Formula (I) wherein X is —NHCH$_2$(CH$_2$)$_n$— may be prepared by treating a compound of the formula:

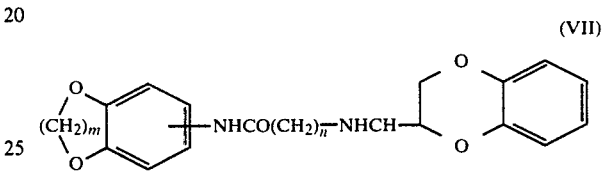 (VII)

wherein m and n are as defined in Formula (I) above, which is obtained by the reaction described in Process 1 above, either as it is or after its acid addition salt has been neutralized, with lithium aluminum hydride in an organic solvent such as tetrahydrofuran.

Specific examples of the compounds according to this invention include:

5-[3-{(1,4-benzodioxan-2-ylmethyl)amino}-2-hydroxy-propoxy]-1,3-benzodioxole;
6-[3-{(1,4-benzodioxan-2-ylmethyl)amino}-2-hydroxy-propoxy]-1,4-benzodioxane;
1-[3-{(1,4-benzodioxan-2-ylmethyl)amino}-2-hydroxy-propoxy]-3,4-trimethylenedioxybenzene;
4-[3-{(1,4-benzodioxan-2-ylmethyl)amino}-2-hydroxy-propoxy]-1,3-benzodioxole;
5-[3-{(1,4-benzodioxan-2-ylmethyl)amino}-2-hydroxy-propoxy]-1,4-benzodioxane;
1-[3-{(1,4-benzodioxan-2-ylmethyl)amino}-2-hydroxy-propoxy]-2,3-trimethylenedioxybenzene;
5-[3-{(1,4-benzodioxan-2-ylmethyl)amino}propoxy]-1,3-benzodioxole;
5-[3-{(1,4-benzodioxan-2-ylmethyl)amino}butoxy]-1,3-benzodioxole;
4-[3-{(1,4-benzodioxan-2-ylmethyl)amino}propoxy]-1,3-benzodioxole;
4-[3-{(1,4-benzodioxan-2-ylmethyl)amino}butoxy]-1,3-benzodioxole;
6-[3-{(1,4-benzodioxan-2-ylmethyl)amino}propoxy]-1,4-benzodioxane;
6-[3-{(1,4-benzodioxan-2-ylmethyl)amino}butoxy]-1,4-benzodioxane;
5-[3-{(1,4-benzodioxan-2-ylmethyl)amino}propoxy]-1,4-benzodioxane;
5-[3-{(1,4-benzodioxan-2-ylmethyl)amino}butoxy]-1,4-benzodioxane;
1-[3-{(1,4-benzodioxan-2-ylmethyl)amino}propoxy]-3,4-trimethylenedioxybenzene;
1-[3-{(1,4-benzodioxan-2-ylmethyl)amino}butoxy]-3,4-trimethylenedioxybenzene;
1-[3-{(1,4-benzodioxan-2-ylmethyl)amino}propoxy]-2,3-trimethylenedioxybenzene;

1-[3-{(1,4-benzodioxan-2-ylmethyl)amino}butoxy]-2,3-trimethylenedioxybenzene;
5-[2-{(1,4-benzodioxan-2-ylmethyl)amino}acetyl]-1,3-benzodioxole;
5-[2-{(1,4-benzodioxan-2-ylmethyl)amino}-1-hydroxyethyl]-1,3-benzodioxole;
6-[2-{(1,4-benzodioxan-2-ylmethyl)amino}acetyl]-1,4-benzodioxane;
6-[2-{(1,4-benzodioxan-2-ylmethyl)amino}-1-hydroxyethyl]-1,4-benzodioxane;
1-[2-{(1,4-benzodioxan-2-ylmethyl)amino}acetyl]-3,4-trimethylenedioxybenzene;
1-[2-{(1,4-benzodioxan-2-ylmethyl)amino}-1-hydroxyethyl]-3,4-trimethylenedioxybenzene;
5-[4-{(1,4-benzodioxan-2-ylmethyl)amino}butyl]-1,3-benzodioxole;
6-[4-{(1,4-benzodioxan-2-ylmethyl)amino}butyl]-1,4-benzodioxane;
1-[4-{(1,4-benzodioxan-2-ylmethyl)amino}butyl]3,4-trimethylenedioxybenzene;
N-[3-{(1,4-benzodioxan-2-ylmethyl)amino}propionyl]-3,4-methylenedioxyaniline;
N-[3-{(1,4-benzodioxan-2-ylmethyl)amino}propyl]-3,4-methylenedioxyaniline;
N-[3-{(1,4-benzodioxan-2-ylmethyl)amino}propionyl]-3,4-dimethylenedioxyaniline;
N-[3-{(1,4-benzodioxan-2-ylmethyl)amino}propyl]-3,4-dimethylenedioxyaniline;
N-[3-{(1,4-benzodioxan-2-ylmethyl)amino}propionyl]-3,4-trimethylenedioxyaniline;
N-[3-{(1,4-benzodioxan-2-ylmethyl)amino}propyl]-3,4-trimethylenedioxyaniline;
6-[3-{(1,4-benzodioxan-2-ylmethyl)amino}propylthio}-1,4-benzodioxane;
1-[3-{(1,4-benzodioxan-2-ylmethyl)amino}propylthio]-3,4-trimethylenedioxybenzene.

The present invention also embraces acid addition salts of the alkylenedioxybenzene derivatives of Formula (I). The acids that can be used to form such addition salts include inorganic acids such as hydrochloric acid, hydrobromic acid, sulfuric acid, phosphoric acid, nitric acid, etc. as well as organic acids such as acetic acid, succinic acid, adipic acid, propionic acid, tartaric acid, fumaric acid, maleic acid, oxalic acid, citric acid, benzoic acid, toluenesuflonic acid, methanesulfonic acid, etc.

As previously mentioned, the compounds of this invention possess hypotensive activities.

The hypotensive activities of the compounds of this invention were tested as follows: The test animals used were spontaneous hypertensive rats (SHR) of 5 to 7 month old weighing 300 to 370 g. The blood pressure and the heart rate were measured bloodily under no anesthesia by means of a cathether which has been inserted through the tail's artery under ether anesthesia, thereby determining the average blood pressure and heart rate before medication.

Thereafter, the test compound was orally administered every hour at a dose of 1, 3 or 10 mg/kg and the hypotensive effect was evaluated. The hypotensive effect was expressed as percent drop relative to the blood pressure before medication. The results are shown in Table 1.

The values for acute toxicity (LD50) were calculated by the Litchfield-Wilcoxon method from the data obtained on mice. The results are shown in Table 2.

As can be seen from Table 1, all the compounds of this invention exert their hypotensive effects satisfactorily at an oral dose of 1 mg/kg and they develop their efficacy rapidly and have long-lasting effects. In addition, as shown in Table 2, the acute toxicity of the compounds is weak. Therefore, in view of their high efficacy developed, it is inferred that they are medicaments of very high safety.

TABLE 1

| | Hypotensive effect (% drop in blood pressure) | | |
|---|---|---|---|
| No.*[1] | 1 mg/kg p.o. | 3 mg/kg p.o. | 10 mg/kg p.o. |
| 1 | 9.9 | 15.4 | 27.6 |
| 2 | 9.0 | 20.2 | 30.4 |
| 5 | | 32.6 | 47.6 |
| 6 | | 28.5 | 32.0 |
| 7 | | 35.2 | 55.3 |
| 9 | | 30.1 | 48.4 |
| 10 | | 30.6 | 40.0 |
| 12 | 20.1 | 28.2 | 42.3 |
| 16 | 12.1 | 33.7 | 50.0 |
| 17 | 20.1 | 29.7 | |
| 18 | 11.9 | 27.5 | 41.0 |
| 19 | 19.6 | 27.8 | 44.3 |
| 21 | 9.8 | 19.5 | 39.1 |
| 26*[2] | | 3.5 | 8.1 |
| 27*[2] | 7.8 | 12.8 | 30.3 |

*[1] The compound numbers are the same as those in Table 3 and the structure of each compound is shown therein.
*[2] Comparative data.

TABLE 2

| No.* | LD$_{50}$ (mice, mg/kg) |
|---|---|
| 1 | 515 (p.o.) |
| 5 | 165 (i.p.) |
| 12 | 1,350 (p.o.) |
| 16 | 31.0 (i.v.) |

*The compound numbers are the same as those given in Table 3 and the structure of each compound is shown therein.

The compounds according to this invention may be administered by any route and both of oral administration and parenteral administration such as subcutaneous injection, intravenous injection, intramuscular injection or intraperitoneal injection are possible.

The dosage may be determined depending on the age, condition and weight of the patient, the type of the concurrent treatment, if any, the frequency of the treatment, the nature of the desired effect, etc.

In general, the daily dose of the active ingredient is 0.1 to 100 mg/kg-body weight, usually 1 to 30 mg/kg-body weight which is administered in one or more portions.

For oral administration, the compounds of this invention are applied in the form of tablets, capsules, dusts, solutions, elixirs or the like, while for parenteral administration they are applied in sterized liquid forms such as solutions or suspensions. When they are used in the above-mentioned dosage forms, a solid or liquid, non-toxic pharmaceutical carrier may be incorporated in the formulations.

An example of the solid carriers is conventional gelatine capsules. The active ingredients may be tabletted or dust-packaged with or without an adjuvant.

These capsules, tablets or dust contains generally 5 to 95%, preferably 25 to 90% by weight of the active ingredient. Thus, each of these dosage forms contains 5 to 500 mg, preferably 25 to 250 mg of the active ingredient.

Useful liquid carriers include water, oils of animal or vegetable origin such as petroleum, peanut oil, soybean oil, mineral oil, sesame oil, and synthetic oils.

In addition, physiological saline, solutions of dextrose or similar sugar and glycols such as ethylene glycol, propylene glycol, polyethylene glycol, etc. are generally suitable for use as liquid carriers. Particularly, injections in which physiological saline is used as carriers usually contain 0.5 to 20%, preferably 1 to 10% by weight of the active ingredient.

Liquid preparations for oral administration are preferably suspensions or syrups containing 0.5 to 10% by weight of the active ingredient. In such cases, water-like excipients such as flavors, syrups, pharmaceutical micelles may be used as carriers.

As stated above, the compounds of this invention are valuable as hypotensives.

Having generally described the invention, a more complete understanding can be obtained by reference to certain specific examples, which are included for purposes of illustration only and are not intended to be limiting unless otherwise specified.

EXAMPLE 1

5-[3-{(1,4-Benzodioxan-2-ylmethyl)amino}-2-hydroxypropoxy]-1,3-benzodioxole hydrochloride A solution of 138.1 g of 3,4-methylenedioxyphenol in 500 ml of N,N-dimethylformamide is added dropwise to a suspension of 50.4 g of 50% sodium hydride in 500 ml of N,N-dimethylformamide under stirring and ice-cooling. Thereafter, 462.5 g of epichlorohydrin is added in one portion. The ice bath is removed and the mixture is stirred for 4 hour at room temperature. The reaction solvent is then distilled off in vacuo and 500 ml of benzene and 200 ml of water are added to the residue. After the aqueous layer is separated, the benzene layers is washed with water and dried over anhydrous sodium sulfate and the benzene is then distilled off in vacuo. The residue is subjected to vacuum distillation to give 151.1 g of an epoxide boiling at 130°-135° C./1 mmHg. Yield: 78%.

To 5.0 g of the epoxide obtained above are added 30 ml of methanol and 4.7 g of 2-aminomethyl-1,4-benzodioxane and the mixture is heated at reflux for 4 hours under stirring. After the reaction solvent is distilled off in vacuo, 100 ml of ethyl acetate and 50 ml of water are added to the residue and the aqueous layer is removed. The ethyl acetate layer is dried over anhydrous sodium sulfate and 5.2 ml of 20% hydrogen chloride in ethanol is added thereto. The precipitated crystals are then collected by filtration and recrystallized from ethanol to give 7.2 g (71%) of 5-[3-{(1,4-benzodioxan-2-ylmethyl)amino}-2-hydroxypropoxy]-1,3-benzodioxole hydrochloride. The characteristics of this compound are shown in Table 3 as Compound 1.

Likewise, Compounds 2 to 4 in Table 3 are prepared in the same way, and their characteristics are shown therein.

EXAMPLE 2

5-[3-{(1,4-Benzodioxan-2-ylmethyl)amino}propoxy]-1,3-benzodioxole hydrochloride

To a solution prepared by dissolving 7.3 g of potassium hydroxide in 7 ml of water and then adding 120 ml of t-butanol are added 15 g of 3,4-methylenedioxyphenol and 88 g of 1,3-dibromopropane and the mixture is stirred for 3 hours under heating at reflux. After completion of the reaction, the solvent is distilled off and benzene is added and washed with water. The benzene layer is dried over anhydrous sodium sulfate and the solvent is distilled off. The residue is subjected to vacuum distillation to give 23 g of 5-(3-bromopropoxy)-1,3-benzodioxole boiling at 120° C./1 mmHg.

To a solution of 5.0 g of 5-(3-bromopropoxy)-1,3-benzodioxole in 30 ml of DMF are added 3.1 g of 2-aminomethyl-1,4-benzodioxane and 3.0 g of triethylamine and the mixture is stirred for 12 hours at 70° C. After completion of the reaction, water is added and the mixture is extracted with ether. The extract is washed with saturated sodium chloride solution and dried over anhydrous sodium sulfate. The solvent is then distilled off and the residue is taken up in alcohol. To the alcoholic solution is added 20% hydrogen chloride in ethanol and the resulting crystals are collected by filtration and recrystallized from alcohol to give 5.5 g (75%) of 5-[3-{(1,4-benzodioxan-2-ylmethyl)amino}propoxy]-1,3-benzodioxole hydrochloride, the characteristics of which are shown in Table 3 as Compound 5.

Likewise, Compounds 6 to 11 in Table 3 are prepared in the same way, and their characteristics are also shown therein.

EXAMPLE 3

5-[2-{(1,4-Benzodioxan-2-ylmelthyl)amino}acetyl]-1,3-benzodioxole hydrochloride

To a solution of 2.0 g of 5-(α-bromoacetyl)-1,3-benzodioxole in 30 ml of tetrahydrofuran are added 1.4 g of 2-aminomethyl-1,4-benzodioxane and 1.5 ml of triethylamine and the reaction is allowed to proceed for 5 hours at room temperature. After completion of the reaction, ethyl acetate is added and the mixture is washed twice with saturated sodium chloride solution and dried over anhydrous sodium sulfate. The solvent is then distilled off and the residue is taken up in ethanol. An ethanolinic solution of hydrogen chloride is then added to cause precipitation of crystals. The crystals are collected by filtration and recrystallized from ethanol to give 2.2 g (73%) of 5-[2-{(1,4-benzodioxan-2-ylmethyl)amino}acetyl]-1,3-benzodioxole hydrochloride.

The characteristics of this compound are shown in Table 3 as Compound 12.

Likewise, Compounds 13 and 14 in Table 3 are prepared in the same way and their characteristics are also shown in Table 3.

EXAMPLE 4

5-[2-{(1,4-Benzodioxan-2-ylmethyl)amino}-1-hydroxyethyl]-1,3-benzodioxole

In 15 ml of methanol is dissolved 1.0 g of 5-[2-{(1,4-benzodioxan-2-ylmethyl)amino}acetyl]-1,3-benzodioxole hydrochloride prepared according to the procedure described in Example 3 and the solution is neutralized with 2N sodium hydroxide. Thereafter, 100 mg of sodium borohydride is added and the mixture is stirred for 6 hours at room temperature. After completion of the reaction, the solvent is distilled off and the residue is dissolved in ethyl acetate and washed twice with saturated sodium chloride solution. After drying over anhydrous sodium sulfate, the solvent is distilled off and the residue is crystallized from water-alcohol to give 800 mg (89%) of 5-[2-{(1,4-benzodioxan-2-ylmethyl)amino}-1-hydroxyethyl]-1,3-benzodioxole.

The characteristics of this compound are shown in Table 3 as Compound 20.

Likewise, Compounds 21 and 22 are prepared in the same way and their characteristics are also shown in Table 3.

EXAMPLE 5

1-[4-{(1,4-Benzodioxan-2-ylmethyl)amino}butyl]-3,4-trimethylenedioxybenzene hydrochloride In 50 ml of dimethylformamide are dissolved 9.8 g of 1-(4-chlorobutyl)-3,4-trimethylenedioxybenzene, 9.1 g of (1,4-benzodioxan-2-ylmethyl)amine and 8 g of triethylamine and the resulting solution is heated under stirring at 80° C. for 45 hours. After completion of the reaction, the solvent is distilled off in vacuo and 2N sodium hydroxide is added. The mixture is extracted with ether and the ether layer is washed with saturated sodium chloride solution and dried over anhydrous sodium sulfate. The solvent is distilled off and the residue is dissolved in ether. To the solution is added 20% hydrogen chloride in ethyl acetate under ice cooling and the resulting crystals are collected by filtration and recrystallized from ethanol to give 10.9 g (61%) of 1-[4-{(1,4-benzodioxan-2-ylmethyl)amino}butyl]-3,4-trimethylenedioxybenzene hydrochloride.

The characteristics of this compound is shown in Table 3 as Compound 17.

Likewise, Compounds 15 and 16 are prepared in the same way and their characteristics are also known in Table 3.

EXAMPLE 6

N-[3-{(1,4-Benzodioxan-2-ylmethyl)amino}propionyl]-3,4-methylenedioxyaniline hydrochloride To a solution of 10 g of N-(3-chloropropionyl)-3,4-methylenedioxyaniline in 50 ml of dimethylformamide are added 8.7 g of 1,4-benzodioxan-2-ylmethylamine and 8.9 g of triethylamine and the mixture is stirred for 20 hours at 50° C. After completion of the reaction, water is added and the mixture is extracted with ethyl acetate. The ethyl acetate layer is washed with saturated sodium chloride solution and dried over anhydrous sodium sulfate and the solvent is distilled off. The residue is dissolved in ethyl acetate and 20% hydrogen chloride in ethyl acetate is added. The resulting crystals are collected by filtration and recrystallized from ethanol to give 13.7 g (77%) of N-[3-{(1,4-benzodioxan-2-ylmethyl)amino}propionyl]-3,4-methylenedioxyaniline.

The characteristics of this compound are shown in Table 3 as Compound 18.

EXAMPLE 7

N-[3-{(1,4-Benzodioxan-2-ylmethyl)amino}propyl]-3,4-methylenedioxyaniline

In 50 ml of tetrahydrofuran is suspended 1.5 g of lithium aluminum hydride and a solution of 6.0 g of N-[3-{(1,4-benzodioxan-2-yl}methyl)amino propionyl]-3,4-methylenedioxyaniline prepared according to the procedure described in Example 6 dissolved in 10 ml of tetrahydrofuran is added dropwise to the suspension. After completion of the dropwise addition, the mixture is stirred for 4 hours at 50° C. After completion of the reaction, the reaction mixture is subjected to the post-treatment for lithium aluminum hydride in the conventional manner and the resulting precipitates including aluminum hydroxide are removed by filtration. The filtrate is concentrated and then dissolved in ethyl acetate and the resulting solution is washed with saturated sodium chloride solution and dried over anhydrous sodium sulfate. Thereafter, 20% hydrogen chloride in ethyl acetate is added and the resulting crystals are collected by filtration and recrystallized from ethanol to give 5.6 g (80%) of N-[3-{(1,4-benzodioxan-2-ylmethyl)amino}propyl]-3,4-methylenedioxyaniline.

The characteristics of this compound are shown in Table 3 as Compound 19.

Likewise, Compound 25 is prepared in the same way and its characteristics are also shown in Table 3.

TABLE 3

| No. | m | Position on the benzene ring to which X is attached | X | Addition salt | m.p. (°C.) | Calculated C | Calculated H | Calculated N | Found C | Found H | Found N |
|---|---|---|---|---|---|---|---|---|---|---|---|
| 1 | 1 | 2 | —OCH$_2$CHCH$_2$—<br>       \|<br>      OH | HCl | 180–4 | 57.65 | 5.60 | 3.54 | 57.54 | 5.55 | 3.38 |
| 2 | 2 | 2 | —OCH$_2$CHCH$_2$—<br>       \|<br>      OH | HCl | 171–5 | 58.61 | 5.90 | 3.42 | 58.73 | 5.97 | 3.37 |
| 3 | 3 | 2 | —OCH$_2$CHCH$_2$—<br>       \|<br>      OH | (CO$_2$H)$_2$ | 150–2 | 57.86 | 5.70 | 2.93 | 57.99 | 5.61 | 3.08 |
| 4 | 1 | 1 | —OCH$_2$CHCH$_2$—<br>       \|<br>      OH | HCl | 173–5 | 57.65 | 5.60 | 3.54 | 57.79 | 5.48 | 3.44 |
| 5 | 1 | 2 | —O(CH$_2$)$_3$— | HCl | 195–8 | 60.08 | 5.84 | 3.69 | 60.16 | 5.79 | 3.79 |
| 6 | 1 | 2 | —O(CH$_2$)$_4$— | HCl | 140–2 | 60.99 | 6.14 | 3.56 | 61.12 | 6.03 | 3.55 |
| 7 | 2 | 2 | —O(CH$_2$)$_3$— | HCl | 151–3 | 60.99 | 6.14 | 3.56 | 60.86 | 6.11 | 3.46 |
| 8 | 1 | 2 | —O(CH$_2$)$_4$— | HCl | 169–171 | 61.84 | 6.42 | 3.43 | 61.71 | 6.63 | 3.28 |
| 9 | 3 | 2 | —O(CH$_2$)$_3$— | HCl | 150–3 | 61.84 | 6.42 | 3.43 | 61.93 | 6.38 | 3.40 |
| 10 | 1 | 1 | —O(CH$_2$)$_4$— | HCl | 135–6 | 60.99 | 6.14 | 3.56 | 60.18 | 6.06 | 3.49 |
| 11 | 1 | 1 | —O(CH$_2$)$_3$— | HCl | 160–1 | 60.08 | 5.84 | 3.69 | 59.87 | 5.89 | 3.81 |

TABLE 3-continued $$\underset{1}{\overset{O}{\underset{O}{\overset{|}{(CH_2)_m}}}}\text{benzene ring}\underset{2}{-}X-NH_2-CH_2-\underset{O}{\overset{O}{\bigcirc}}$$

| No. | m | Position on the benzene ring to which X is attached | X | Addition salt | m.p. (°C.) | Calculated C | Calculated H | Calculated N | Found C | Found H | Found N |
|---|---|---|---|---|---|---|---|---|---|---|---|
| 12 | 1 | 2 | —C(O)CH$_2$— | HCl | 188–191 | 59.21 | 5.08 | 3.76 | 59.43 | 4.99 | 3.85 |
| 13 | 2 | 2 | —C(O)CH$_2$— | (CO$_2$H)$_2$ | 191–4 | 58.71 | 4.98 | 3.07 | 58.46 | 4.91 | 3.25 |
| 14 | 3 | 2 | —C(O)CH$_2$— | (CO$_2$H)$_2$ | 171–5 | 59.08 | 5.33 | 3.21 | 59.32 | 5.21 | 3.14 |
| 15 | 1 | 2 | —(CH$_2$)$_4$— | HCl | 212–5 | 63.73 | 6.45 | 3.63 | 63.57 | 6.40 | 3.71 |
| 16 | 2 | 2 | —(CH$_2$)$_4$— | HCl | 163–6 | 64.59 | 6.73 | 3.64 | 64.36 | 6.69 | 3.57 |
| 17 | 3 | 2 | —(CH$_2$)$_4$— | HCl | 178–9 | 65.28 | 7.17 | 3.36 | 65.10 | 6.95 | 3.45 |
| 18 | 1 | 2 | —NHCO(CH$_2$)$_2$— | HCl | 224–5 | 58.09 | 5.39 | 7.13 | 57.81 | 5.45 | 7.01 |
| 19 | 1 | 2 | —NH(CH$_2$)$_3$— | 2HCl | 206–210 | 54.95 | 5.82 | 6.74 | 55.23 | 5.93 | 6.80 |
| 20 | 1 | 2 | —CH(OH)CH$_2$— | — | 99–100 | 66.65 | 6.03 | 3.93 | 66.46 | 6.16 | 4.08 |
| 21 | 2 | 2 | —CH(OH)CH$_2$— | — | 121–4 | 67.48 | 6.40 | 3.81 | 67.21 | 6.49 | 3.92 |
| 22 | 3 | 2 | —CH(OH)CH$_2$— | — | 94–6 | 60.18 | 5.44 | 3.67 | 60.40 | 5.34 | 3.71 |
| 23 | 2 | 2 | —S(CH$_2$)$_3$— | HCl | 124–7 | 58.60 | 5.90 | 3.42 | 58.45 | 5.83 | 3.46 |
| 24 | 3 | 2 | —S(O)(CH$_2$)$_3$— | HCl | 130–3 | 57.33 | 5.96 | 3.18 | 57.09 | 5.83 | 3.23 |
| 25 | 3 | 2 | —NH(CH$_2$)$_3$— | 2HCl | 217–222 | 56.89 | 6.37 | 6.32 | 56.61 | 6.45 | 6.19 |
| 26* | 1 | 1 | —O(CH$_2$)$_2$— | HCl | 205–7 | 59.10 | 5.51 | 3.83 | 58.89 | 5.63 | 3.90 |
| 27* | 1 | 2 | —C(O)CH$_2$CH$_2$— | HCl | 189–192 | 60.18 | 5.44 | 3.67 | 60.40 | 5.34 | 3.71 |

*Comparative example

The following compounds can be prepared in the same manner as disclosed in the above examples:

N-[3-{(1,4-benzodioxan-2-ylmethyl)amino}propyl]-N-methyl-3,4-methylenedioxyaniline
N-[4-{(1,4-benzodioxan-2-ylmethyl)amino}butyl]-N-propyl-3,4-trimethylenedioxyaniline
N-[3-{(1,4-benzodioxan-2-ylmethyl)amino}propyl]-N-acetyl-3,4-methylenedioxyaniline
N-[4-{(1,4-benzodioxan-2-ylmethyl)amino}butyl]-N-formyl-3,4-dimethylenedioxyaniline
N-[4-{(1,4-benzodioxan-2-ylmethyl)amino}butyl]-3,4-methylenedioxyaniline
N-[4-{(1,4-benzodioxan-2-ylmethyl)amino}butyryl]-3,4-trimethylenedioxyaniline
1-[3-{(1,4-benzodioxan-2-ylmethyl)amino}propyl]sulfinyl-3,4-trimethylenedioxybenzene
1-[3-{(1,4-benzodioxan-2-ylmethyl)amino}propyl]sulfonyl-3,4-trimethylenedioxybenzene
N-[3-{(1,4benzodioxan-2-ylmethyl)amino}propyl]-N-methyl-3,4-dimethylenedioxyaniline
N-[3-{(1,4-benzodioxan-2-ylmethyl)amino}propyl]-N-methyl-3,4-trimethylenedioxyaniline
N-[3-{(1,4-benzodioxan-2-ylmethyl)amino}propyl]-N-acetyl-3,4-dimethylenedioxyaniline
N-[3-{(1,4-benzodioxan-2-ylmethyl)amino}propyl]-N-acetyl-3,4-trimethylenedioxyaniline
6-[3-{(1,4-benzodioxan-2-ylmethyl)amino}propyl]sulfinyl-1,4-benzodioxane.

Having now fully described the invention, it will be apparent to one of ordinary skill in the art that many changes and modifications can be made thereto without departing from the spirit or scope of the invention as set forth herein.

What is claimed as new and intended to be covered letters patent is:

1. An alkylenedioxybenzene compound of the formula:

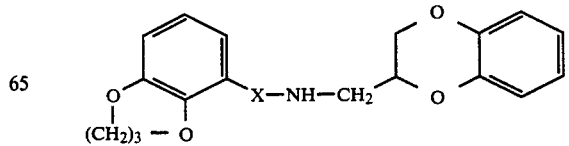

wherein X is —O(CH$_2$)$_3$—, —O(CH$_2$)$_4$—, —NH(CH$_2$)$_3$—, —NH(OH$_2$)$_4$—, —(CH$_2$)$_4$—,

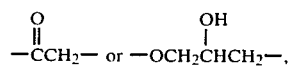

or an acid addition salt thereof.

2. The compound of claim 1, of the formula:

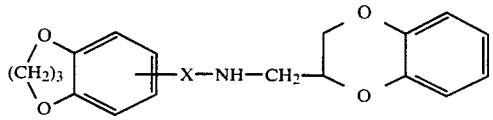

wherein X is —O(CH$_2$)$_3$—, —O(CH$_2$)$_4$—, —NH(CH$_2$)$_3$—, —NH(CH$_2$)$_4$—, —(CH$_2$)$_4$—,

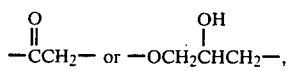

or an acid addition salt thereof.

3. The compound of claim 1, which is 1-[3-{(1,4-benzodioxan-2-ylmethyl)amino}propoxy]-3,4-trimethylenedioxybenzene.

4. The compound of claim 1, which is 1-[3-{(1,4-benzodioxan-2-ylmethyl)amino}-2-hydroxypropoxy]-3,4-trimethylenedioxybenzene.

5. The compound of claim 1, which is N-[3-{(1,4-benzodioxan-2-ylmethyl)amino}propyl]-3,4-trimethylenedioxyaniline.

6. The compound of claim 1, which is 1-[4-{(1,4-benzodioxan-2-ylmethyl)amino}butyl]-3,4-trimethylenedioxybenzene.

7. 5-[3-{(1,4-Benzodioxan-2-ylmethyl)amino}propoxy]-1,3-benzodioxole.

8. 4-[3-{(1,4-Benzodioxan-2-ylmethyl)amino}propoxy]-1,3-benzodioxole.

9. 6-[3-{(1,4-Benzodioxan-2-ylmethyl)amino}propoxy]-1,4-benzodioxane.

10. N-[3-{(1,4-Benzodioxan-2-ylmethyl)amino}propyl]-3,4-methylenedioxyaniline.

11. 5-[2-{(1,4-Benzodioxan-2-ylmethyl)amino}acetyl]-1,3-benzodioxole.

12. 6-[3-{(1,4-Benzodioxan-2-ylmethyl)amino}-2-hydroxypropoxy]-1,4-benzodioxane.

* * * * *